United States Patent [19]

Stover et al.

[11] Patent Number: 5,196,906

[45] Date of Patent: Mar. 23, 1993

[54] MODULAR SCATTEROMETER WITH INTERCHANGEABLE SCANNING HEADS

[75] Inventors: John C. Stover; James A. Bender; Marvin L. Bernt; Donald R. Bjork; Paul D. Chaussé; Daniel R. Cheever; Kelly H. Kirchner; Tod F. Schiff; Vincent C. Skurdal, all of Bozeman, Mont.

[73] Assignee: TMA Technologies, Inc., Bozeman, Mont.

[21] Appl. No.: 547,468

[22] Filed: Jun. 29, 1990

[51] Int. Cl.$^5$ .......................................... G01N 21/47
[52] U.S. Cl. .................................................... 356/446
[58] Field of Search ................................ 356/445–448, 356/237

[56] References Cited

U.S. PATENT DOCUMENTS

| | | | |
|---|---|---|---|
| 2,830,490 | 4/1958 | Pelegrini | 356/72 |
| 3,327,583 | 6/1967 | Vanderschmidts et al. | 356/51 |
| 3,421,821 | 1/1969 | Allessi | 356/445 |
| 3,473,878 | 10/1969 | Schweitzer | 356/446 |
| 3,496,359 | 2/1970 | Weinstock et al. | 250/358.1 |
| 3,746,869 | 7/1973 | Lindstedt et al. | 240/218 |
| 3,771,880 | 11/1973 | Bennett | 356/209 |
| 3,971,956 | 7/1976 | Jakeman et al. | 250/571 |
| 4,072,426 | 2/1978 | Horn | 356/212 |
| 4,097,160 | 6/1978 | Yataki et al. | 356/237 |
| 4,156,571 | 5/1979 | Ljung | 356/445 |
| 4,218,144 | 8/1980 | Whitehouse et al. | 356/446 |
| 4,269,518 | 5/1981 | Rahn | 356/445 |
| 4,360,275 | 11/1982 | Louderback | 356/446 |
| 4,365,896 | 12/1982 | Mihalow | 356/446 |
| 4,373,819 | 2/1983 | Pallotta | 356/446 |
| 4,402,613 | 9/1983 | Daly et al. | 356/446 |
| 4,484,819 | 11/1984 | Ulrich | 356/446 |
| 4,552,458 | 11/1985 | Lowne | 356/446 |
| 4,583,861 | 4/1986 | Yamaji et al. | 356/446 |
| 4,607,955 | 8/1986 | Corbett | 356/342 |
| 4,632,561 | 12/1986 | Rosencwaig et al. | 356/432 |
| 4,687,338 | 8/1987 | Task et al. | 356/446 |
| 4,750,822 | 6/1988 | Rosencwaig et al. | 356/445 |
| 4,761,676 | 8/1988 | Wiles et al. | 356/445 |
| 4,859,062 | 8/1989 | Thura | 356/371 |
| 4,933,567 | 6/1990 | Silva et al. | 250/572 |

OTHER PUBLICATIONS

Timmerman, "Field Measurement of Windshield Surface Areas", SAE Technical Paper, 1986.
Hartmann, "Field Test Method to Determine Window Replacement Criteria for Optical Systems", May 1984.
Stover, "Optical Scatter", Lasers & Optronics, Jul. 1988, vol. 7, No. 7.
TMA QuickScan Scatterometer Brochure, TMA Technologies, Inc.
TMA CASI Scatterometer Brochure, TMA Technologies, Inc.
TMA Scatter Measurement Brochure, TMA Technologies, Inc.
TMA Scatter Analysis Software Brochure, TMA Technologies, Inc., Aug. 1989.
Stover, et al., "Comparison of BRDF Data from Two Scatterometers," Proc. SPIE, vol. 818, Current Developments in Optical Engineering II, p. 68 (1987d).
Rifkin, et al, "Design Review of a Complete Angle Scatter Instrument," Proc. SPIE, vol. 1036-15 (1988).
Stover, "Roughness Characterization of Smooth Machined Surfaces by Light Scattering," Applied Optics, vol. 14, #8, Aug., 1975 (pp. 1796-1802).
Stover, et al., "Calculation of Surface Statistics From Light Scatter", Optical Engineering, Jul./Aug. 1984, V23, #4, pp. 406–412.
Stover, et al., "Design Review of Three Reflectance Scatterometers", SPIE, vol. 362, 1983 (pp. 172–179).

Primary Examiner—Davis L. Willis
Assistant Examiner—K. P. Hantis
Attorney, Agent, or Firm—Dorsey & Whitney

[57] ABSTRACT

An optical measurement device produces quality light scatter measurements using Bidirectional Reflective Distribution Function (BRDF) techniques to analyze data generated from an accurate, portable, relatively inexpensive scatterometer. The scatterometer is provided with interchangeable scanning heads, each scanning head being equipped with ROM data storage containing certain configuration information about the scanning head. The use of the interchangeable scanning heads allows the present invention to make measurements of light scatter for a wide variety of applications and samples under a variety of environmental conditions where scatter measurement has previously not been feasible.

19 Claims, 10 Drawing Sheets

MODULAR SCATTEROMETER WITH INTERCHANGEABLE SCANNING HEADS

TECHNICAL FIELD

This invention relates generally to the field of optical measurement devices. More particularly, the present invention relates to a scatterometer for measuring the amount of light scattered from a sample surface and/or bulk, and then analyzing this information to provide optical performance information, surface roughness statistics, contamination levels, and defect characteristics.

BACKGROUND ART

Many devices are presently used to measure light reflected from or transmitted through a surface in an attempt to determine certain qualities or characteristics of the subject surface and/or bulk. These types of optical measurement devices have a wide variety of applications, including: defect detection, quality control, and contamination assessment for surfaces and bulk materials such as mirrors, windows, semiconductors, crystals, coated surfaces, etc. In general, the prior art devices in this field can be classified into one of two categories: (1) expensive, accurate, research measurement devices; and (2) inexpensive, relatively inaccurate, field comparison devices.

The optical research measurement devices are large, relatively expensive apparatus having measurement volumes that exceed several cubic feet and costing between $50,000 to $500,000. These devices are usually permanently mounted on an optical table and employ computer controlled mechanical stages for measuring the reflected light from the sample. Because of the precise nature of the measurements, these type of apparatus require careful alignment and may take several hours to complete an entire set of measurements for a sample. In current state-of-the-art devices, the data measured using an optical research measurement device is generally presented in a nationally recognized format referred to as the Bidirectional Reflectance Distribution Function (BRDF). Some of these systems are also capable of further data analysis to provide sample characteristics, such as surface roughness.

Examples of these types of optical research measurement devices include a variety of custom built research measurement instruments for use in various industry and government optical laboratories as shown, for example, in U.S. Pat. Nos. 3,771,880, 3,971,956, 4,156,571, 4,360,275 and 4,859,062. Several research measurement scatterometers are also available from Breault Research Organization. The assignee of the present invention, TMA Technologies, Inc., also provides two types of optical research measurement instruments: the CA-SI ™ line of instruments and the QwikScan ™ line of instruments. In addition, several semiconductor manufacturers have created optical research measurement devices to determine the surface characteristics of semiconductor substrates, as shown, for example, in U.S. Pat. Nos. 4,097,160, 4,402,163, 4,583,861 and 4,632,561.

The inexpensive and less accurate field comparison devices generally perform some type of relative comparison whereby the value obtained by the comparison device is compared to a known good sample, rather than determining an absolute measurement of light intensity. Because the data from this type of device is taken in such a manner to make a relatively quick and inexpensive comparison determination, it is not possible to present the data in the BRDF format. Hence, no meaningful data analysis is possible other than the relative comparison determination.

Examples of these types of field comparison devices include surface quality systems developed to monitor material quality during manufacturing. Generally, such systems employ a scanning beam, and compare the relative signal changes with the signal from a known good sample to indicate the presence of a flaw. Examples of field comparison devices that use scattered light as a comparison to test windshields, for example, include a stray light measuring device as described in the SAE Technical Paper by A. Timmermann and G. Gehring, entitled "Field Measurement of Windshield Surface Wear" (September 1986), and U.S. Pat. Nos. 3,771,877 and 4,687,338. A variety of reflectometers have also been used as comparison devices for making simple optical comparisons, including U.S. Pat. Nos. 3,473,878, 4,373,819 and 4,552,458 and a paper by R. Hartman entitled "Field Test Method to Determine Window Replacement Criteria for Optical Systems" (May 1984).

Although present optical measurement devices have proven satisfactory for many applications, it would be desirable to provide an accurate, portable and relatively inexpensive measurement device for measuring light scatter that is capable of making accurate, absolute measurements, presenting data in BRDF format, and analyzing data to provide needed sample characteristics. In addition, it would be advantageous if such a device were capable of making measurements of light scatter for a wide variety of applications under a variety of environmental conditions.

SUMMARY OF THE INVENTION

The present invention provides an optical measurement device that can produce quality light scatter measurements expressed in BRDF format generated from an accurate, portable, relatively inexpensive scatterometer. The scatterometer of the present invention is also provided with interchangeable scanning heads, each scanning head being equipped with means for storing certain configuration information about the scanning head. The use of interchangeable scanning heads allows the present invention to make measurements of light scatter for a wide variety of applications under a variety of environmental conditions and allows direct analysis of results because the measurement data is expressed in BRDF format.

In the preferred embodiment of the present invention, the scatterometer comprises a base unit and one or more interchangeable scanning heads. The base unit includes a rechargeable battery power supply, a Central Processing Unit (CPU) with associated Liquid Crystal Display (LCD), and an Input/Output Port (IOP) for entering operator information to control the scatterometer and transfer information between the CPU and the currently connected scanning heads. The interchangeable scanning heads include one or more light sources and associated optics for producing the light beam that will be reflected off the subject sample surface, one or more detector means for measuring the light scatter, and may be configured with a beam dump at the specular angle direction for measuring the intensity of the reflected light beam. As used within the present invention, the term light includes electromagnetic radiation from the ultra-violet (UV) to the mid infrared (IR), e.g. wavelengths from 0.25 to 14 microns.

The preferred embodiment of the interchangeable scanning heads uses laser diodes as the light sources and silicon detectors to measure the scattered light. It will be recognized, however, that a variety of types of light sources and detectors may be used with the present invention. Examples of suitable light sources include external lasers, light emitting diodes (LED) and broadband thermal sources. Detectors that may be used include silicon and germanium photo diodes, pyroelectric detectors, thermo-electrically cooled diodes, such as indium antimonide and mercury manganese telluride, as well as many others. It will also be recognized that the positioning of the light sources and detectors can be modified to obtain various configurations. For example, some scanning heads might use a linear detector array to record the scatter field, whereas other scanning heads might use an area detector array to record the scanning field.

The interchangeable scanning heads also include a means for storing certain configuration data that describe the particular characteristics and other set-up parameters of the scanning head. These interchangeable scanning heads are operably connected with the base unit via a shielded cable. The cable includes means for transmitting the actual analog voltage signals received by the detector means directly to the microprocessor in the base unit for analog-to-digital conversion and analysis, as well as means for transmitting and receiving digital signals between the interchangeable scanning head and the base unit.

An objective of the present invention is to provide an accurate, portable and relatively inexpensive optical measurement device for measuring light scatter that is capable of making accurate, absolute measurements.

Another objective of the present invention is to provide an accurate, portable and relatively inexpensive optical measurement device for measuring light scatter that is capable of presenting data in BRDF format and analyzing the data to provide needed sample characteristics.

A further objective of the present invention is to provide an optical measurement device capable of making measurements of light scatter for a wide variety of applications under a variety of environmental conditions.

Another objective of the present invention is to provide a modular scatterometer having interchangeable scanning heads that can be individually adapted for scanning different types of measurement needs.

Still another objective of the present invention is to provide a modular scatterometer having interchangeable scanning heads, each scanning head having means for storing information about the head configuration and the sample scatter data.

A further objective of the present invention is to provide scatter data in BRDF format so that it can be directly compared to data obtained from expensive, larger research measurement systems.

A still further objective of the present invention is to allow for analysis of BRDF data to provide information such as surface roughness and defect characteristics without requiring that reference samples be transported to expensive, non-portable, research measurement instruments.

These and other objectives of the present invention will become apparent with reference to drawings, the detailed description of the preferred embodiment and the appended claims.

DESCRIPTION OF THE PREFERRED EMBODIMENTS

Figure 1:
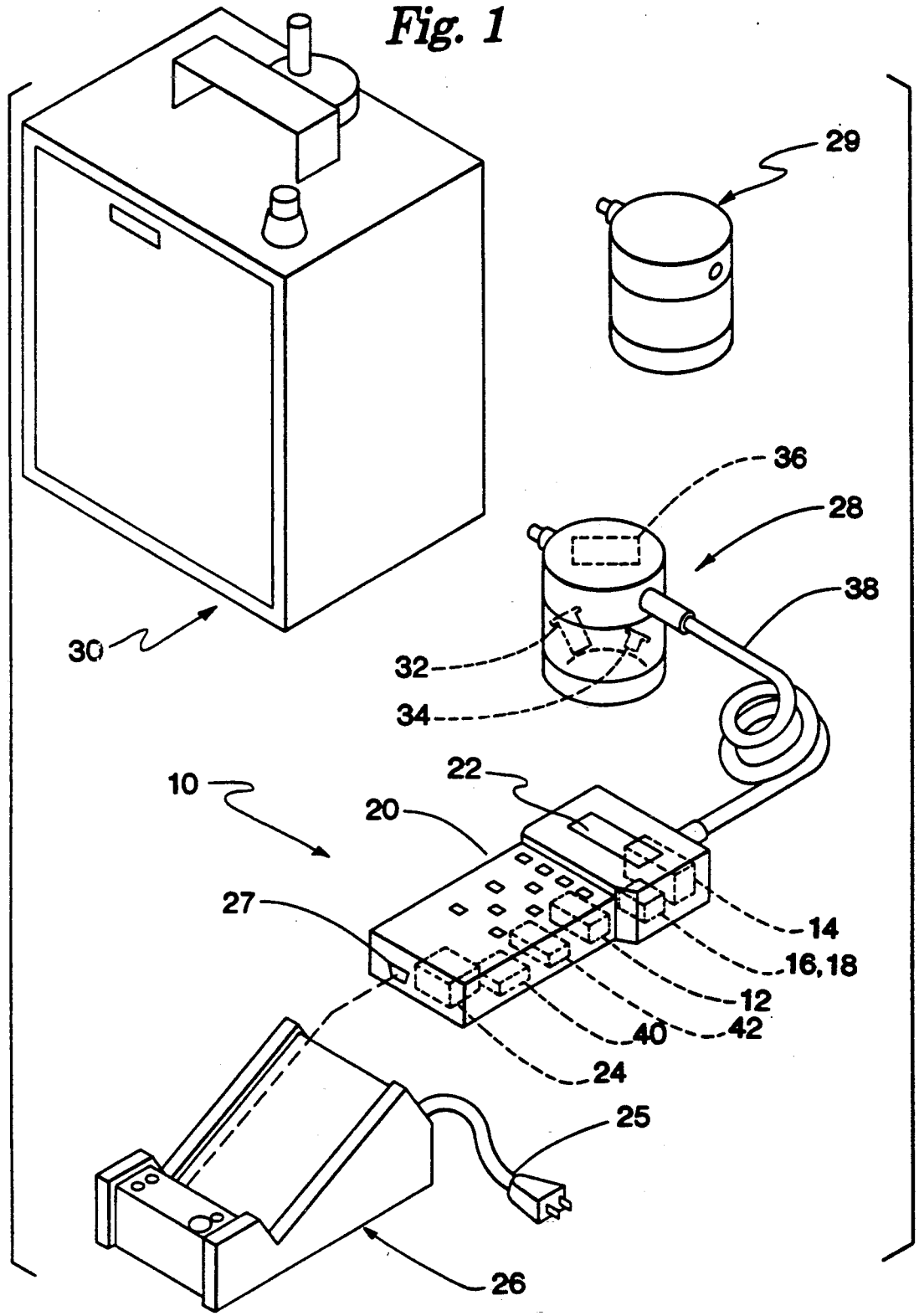
FIG. 1 is an isometric view of the preferred embodiment of scatterometer of the present invention with an interchangeable scanning head attached to the base unit and also showing additional interchangeable scanning heads.

FIG. 1 shows a pictorial view of the preferred embodiment of the modular, portable handheld scatterometer of the present invention. Unlike prior art portable, handheld optical comparison devices, the present invention can produce quality direct light scatter measurements expressed in Bidirectional Reflective Distribution Function (BRDF) format on a variety of surfaces utilizing one of a plurality of interchangeable scanning heads. For a more detailed description of the technical basis for and description of BRDF optical measurements, reference is made to Stover, J., "Optical Scatter", Lasers & Optronics, Vol. 7, No. 8, pp. 61–62; 65–69 (August 1988), a copy of which is attached as an appendix and the disclosure of which is incorporated herein by reference.

From a single, direct light measurement, the present invention can be used to determine both the scattered light level and the RMS roughness on either flat or curved surfaces under most any lighting and environmental conditions. Because the present invention determines a single, direct light measurement for each detector, it will be appreciated that this measurement can be expressed in a variety of ways and still be within the scope of the present invention. For example, instead of expressing the light measurement in terms of BRDF, it would be possible to conversely express the light measurement in terms of BTDF (bidirectional transmissive distribution function), or a combination of both BRDF and BTDF. As such, it will be seen that the present invention is capable of both reflective and transmissive measurements, both in-plane and out-of-plane. Other formats for expressing the light measurement, such as power spectral density (PSD), total integrated spectrum (TIS), RMS roughness or subsurface damage inspection, can also be performed by the present invention. For example, RMS roughness may be calculated over a user specified bandwidth from the BRDF data.

Referring to FIG. 1, a base unit 10 embodies a central processing unit means or CPU 12 which is controlled by a stored program contained in an EPROM 14. The base unit 10 also contains a dynamic storage memory 16 which, in the preferred embodiment, has its own internal battery power means 18 to prevent loss of data. A multi-keypad 20 provides an operator interface means by which to operate the base unit 10. In the preferred embodiment, the multi-keypad 20 includes selectable options that allow for menu selections, entering of data constants, initiation of diagnostics to name some features of the preferred embodiment.

Alphanumeric information is presented to the operator by means of a liquid crystal display (LCD) 22. In the preferred embodiment, four lines of information can be displayed simultaneously. Power for the preferred embodiment of the base unit 10 is provided by rechargeable batteries 24. The rechargeable batteries 24 may be recharged when the base unit 10 is placed in a charger stand 26. In this embodiment, a nine-pin connector 27 is the means for transferring charging energy from the charger stand 26 to the rechargeable batteries 24. The charging stand 26 obtains its electrical energy from standard 120 volt AC, 60 Hz current conducted by power cable 25.

Obtaining accurate light scatter measurements in the preferred embodiment is accomplished by manually holding one of the several selectable, interchangeable scanning heads 28, 29 in physical contact with the surface to be measured. FIG. 1 also shows another version 30 of an interchangeable scanning head in which the sample itself can be placed inside the scanning means. It will be understood that there can be many different types of interchangeable scanning heads having configurations based upon the intended use or application of the present invention. For purposes of describing the preferred embodiment of the present invention three different interchangeable scanning heads 28, 29 and 30 will be described. As shown for scanning head 28, a light source 32 and one or more detectors 34 provide the light and determine the scattering of that light necessary to obtain the desired light measurement data. The amount of scattered light measured by the detector or detectors 34 as power is converted to an analog voltage. This analog voltage is amplified and filtered by an electronic interface circuit card 36. The selected scanning head 28 is connected to the base unit 10 via a universal cable 38. The universal cable 38 passes information from the electronic interface circuit card 36 to an I/O port (IOP) 42 in the base unit 10. The base unit 10 also includes means to convert analog voltages received at the IOP 42 to digital format utilizing an A/D converter 40.

Figure 2:
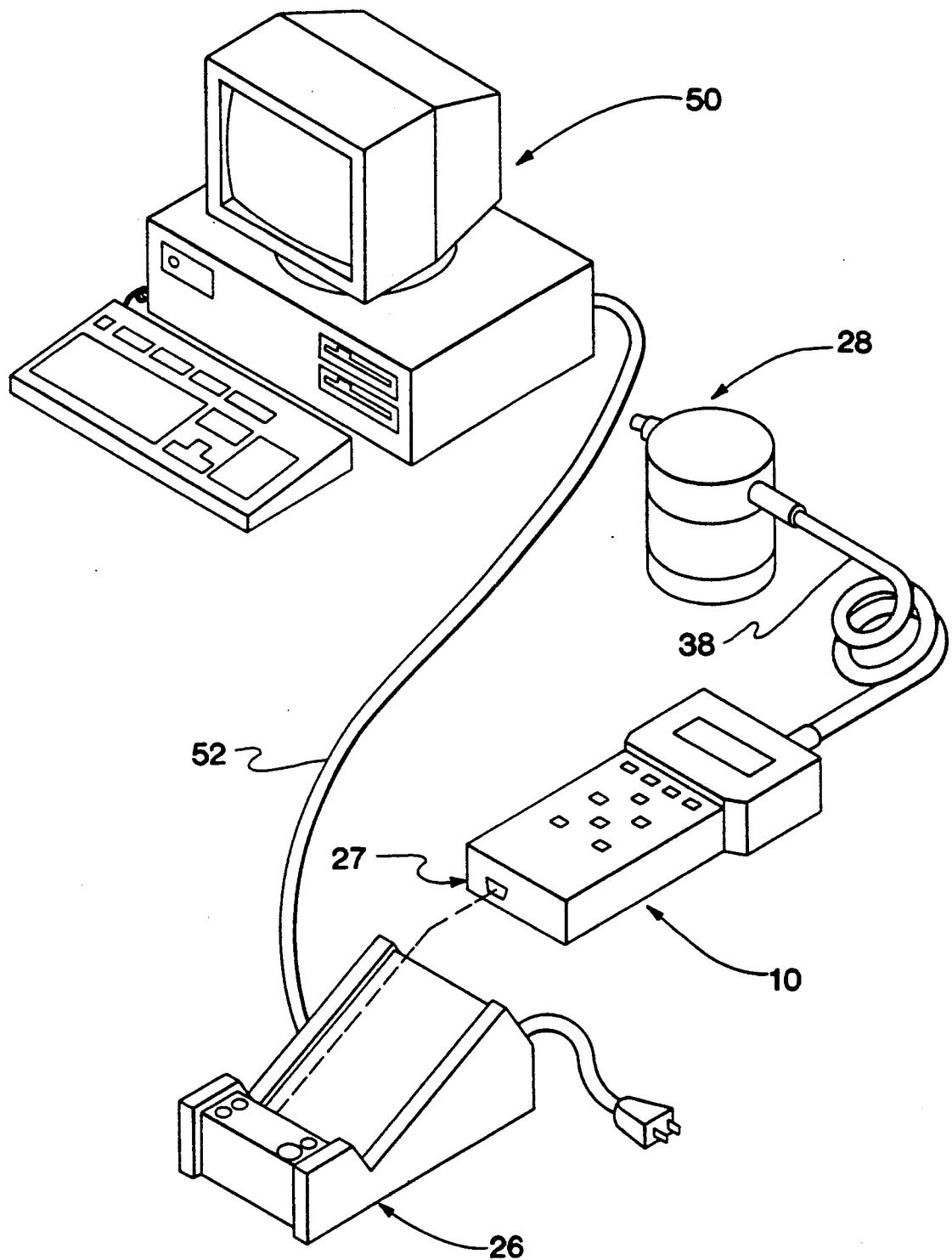
FIG. 2 is an isometric view of an alternative embodiment showing the showing the scatterometer with an attached personal computer (PC).

Referring now to FIG. 2, an alternate embodiment of the present invention will be described. In this embodiment, an independent workstation or personal computer (PC) 50 is connected to the base unit 10 through a serial data cable 52 connected between the PC 50 and the charger stand 26. Serial data information is thus transferred to the CPU 12 through the charger stand 26 via the data port/charger connector 27. This alternate embodiment provides means to store and retieve data and information from the PC 50 for use in the CPU 12. Also, information in the CPU 12 can be stored in the PC 50. In this version of the alternate embodiment, data measured by the base unit 10 can be compared to other data taken at previous times or to data from other samples. In this way changes in the surface sample being measured can be analyzed over a given time period, for example. It will be understood that the PC 50 can be provided with any number of available statistical or customized programs to analyze and compare measured or calculated data.

In the preferred embodiment of the present invention, the CPU 12 is a 80C31 available from Intel Corporation of Santa Clara, CA. The EPROM 14 is a NMC27C512AQ EPROM available from National Semiconductor Corporation of Santa Clara, CA., the static RAM 16 is a MCM60L256A static RAM available from Motorola Semiconductor Products. Inc. of Austin, TX. and the battery backup 18 for the static RAM 16 is a DS1216C battery backup available from Dallas Semiconductor of Dallas, TX. The A/D converter 40 is an ADC0808 A/D converter from Texas Instruments of Dallas, TX. The I/O port 42 is constructed using 74HCT245 and 74HCT273 circuits available from National Semiconductor Corporation of Santa Clara, CA.

Figure 3:
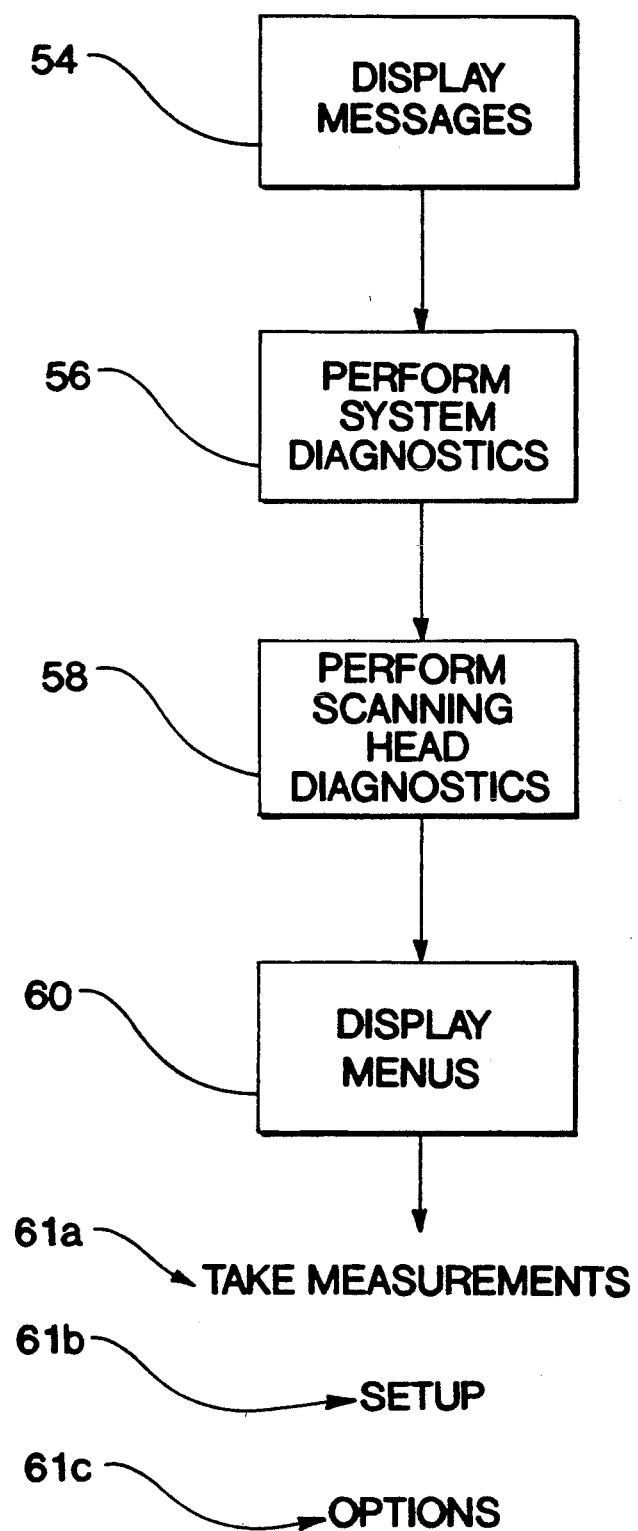
FIG. 3 is a flow diagram of the primary operational functions of the present invention.

With reference to FIG. 3, the block diagram of the operational flow of the present invention will be described. The base unit 10 causes messages 54 to be displayed by means of the LCD 22. These messages 54 are displayed whenever the base unit 10 is turned on and provide information about the base unit 10, such as the serial number, available memory status or time since last calibration. The second operational function is system diagnostics 56. Diagnostics are performed to insure that the base unit 10 is operating properly so that no measurement data will be taken if the diagnostics tests 56 fail. In the preferred embodiment, the diagnostics tests 56 include a system voltage to verify nominal system voltages, a memory test of the static RAM 16 and a check of the functionality of the multi-keypad 20. The head diagnostic block 58 performs diagnostic operations to insure that one of several selectable scanning heads 28, 29, 30 is installed and currently connected to the CPU 12. The manner in which the CPU 12 interrogates the currently connected one of the scanning heads 28, 29, 30 as part of the head diagnostic block 58 is described in greater detail in connection with the description of FIG. 5. This completes the diagnostic sequence. It will be recognized that these and other diagnostic routines that are well known in the art may be performed as part of the diagnostic test 56 and the head diagnostic block 58.

At this point, the base unit 10 is operational and data measurements can begin. The main menu 60 is now presented on the LCD 22. Main menu 60 entries include: Take Measurements 61a, Setup 61b and Options 61c. The operation of Take Measurements 61a is described in greater detail hereinafter in connection with the description of FIG. 6. The Setup option 61b allows the operator to add, delete or change sample labels for the data measurements to be taken. Options 61c is the third selectable function in the menu list 60. Options 61c allows the operator to access the PC 50 through the serial IOP 27 for transferring information to a PC 50, or run diagnostics or obtain a summary of data values previously obtained and stored in the base unit 10.

Figure 4:
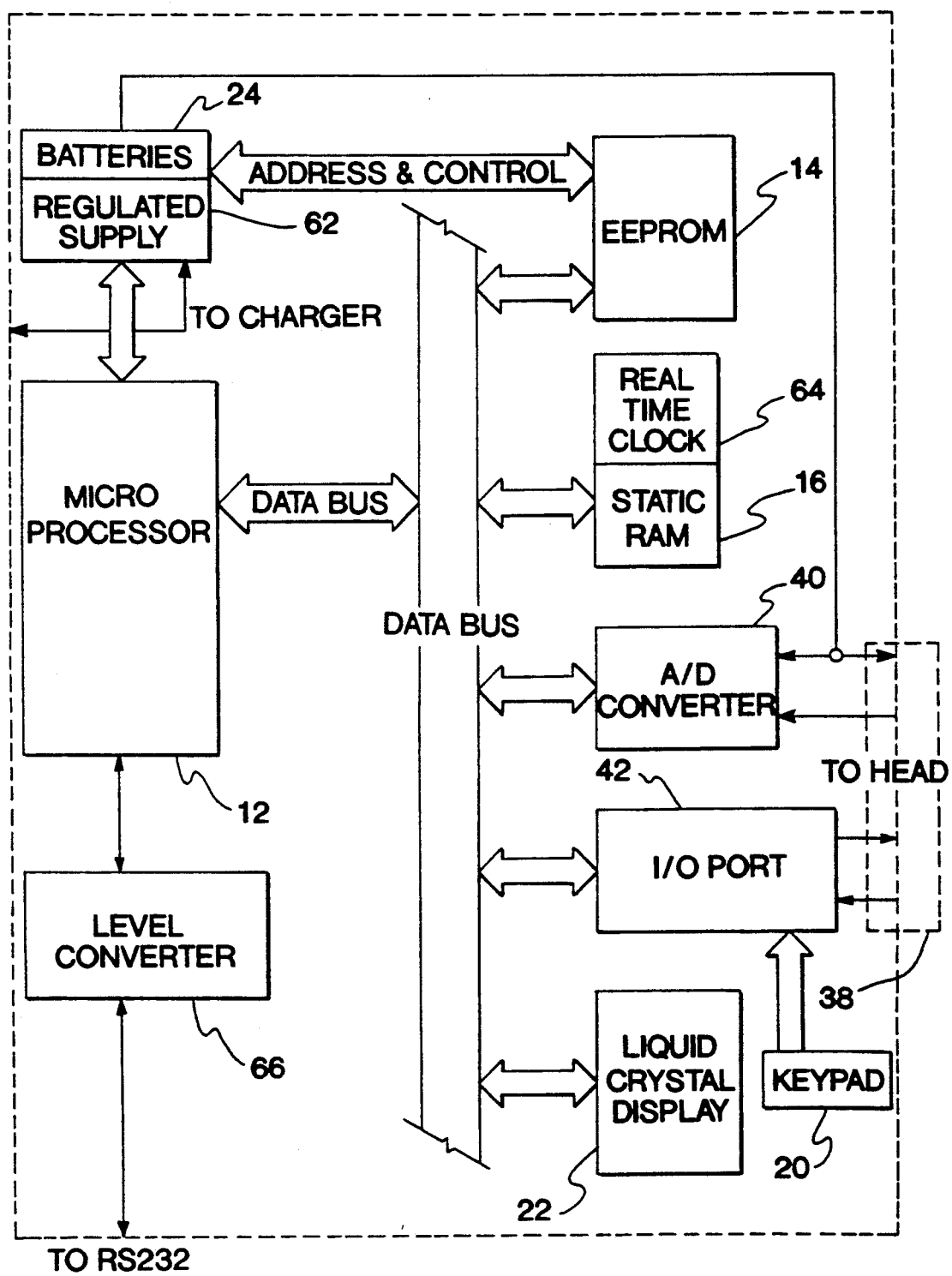
FIG. 4 is an electrical block diagram of the base unit showing the interconnections of the major functional components within the base unit.

FIG. 4 shows how major functional components in the base unit 10 are related for information and data transfer. Operator control is provided by the multi-keypad 20 in the preferred embodiment. Input selections via the multi-keypad 20 are connected to a parallel input/output port (IOP) 42. The parallel IOP 42 provide means for receiving data from the multi-keypad 20. In the preferred embodiment, the IOP 42 also provides means for transferring information into and out of the base unit 10 from the currently attached scanning head 28 via the universal cable 38. Commands from the multi-keypad 20 instruct the firmware program located in the EPROM 14 what function is requested by the operator. For example, menu commands may be required to be displayed in the LCD 22. Although in the preferred embodiment, the LCD 22 is a 20 character by 4 line display, it will be recognized that some applications will require only a single line to just display data or that an alternative embodiment might make use of a graphics display to show BRDF on a continuous graphical basis.

The multi-keypad 20 function can cause data to be read by the currently connected scanning head 28, 29 or 30. The analog voltage data would be present on A/D converter 40 input line on two channels. The universal cable 38 can transfer a signal from the remote switch on the currently connected scanning head 28, 29 or 30. This switch is electrically in parallel with a similar command from the multi-keypad 20.

The A/D converter 40 has 8 channel capacity with 8 bit accuracy. In the preferred embodiment, only 4 channels are utilized. Two of these utilized channels are used to monitor battery 24 level and regulated supply voltage 62 level. If the rechargeable battery 24 voltage is too low, then the preferred embodiment will not allow scatter readings to be taken, and a diagnostic message is presented and the system automatically powers down. The base unit 10 circuits are operated on a regulated 5 volt supply 62. There are 2 channels from the selected scanning head 28 assembly to the A/D 40. During operation of the data acquisition mode, all signals on the universal cable 38, other than the 2 channels connected to the A/D 40, are quieted to allow for the most precise transfer and conversions of the analog signal levels detected by the selected scanning head 28.

In the preferred embodiment of the present invention, 8 bit accuracy is sufficient because of the use of linear gain stages in the scanning head electronics 36. It will be recognized, however, that higher accuracy A/D converters 40 may also be used. In addition, it is also possible to place the A/D converter 40 circuit in the interchangeable scanning heads 28, 29, 30, rather than in the base unit 10. Although this configuration would be more expensive, it would make it possible to reduce the number of lines to the selected scanning head 28 and also to transfer data in digital rather than analog form.

The real time clock 64 is used to provide time and date signature for measurements. The level converter 66 converts the 0-5 v TTL voltage levels to +12 v, -12 v for use in RS232 circuits. All functions are controlled by the micro processor CPU 12.

Figure 5:
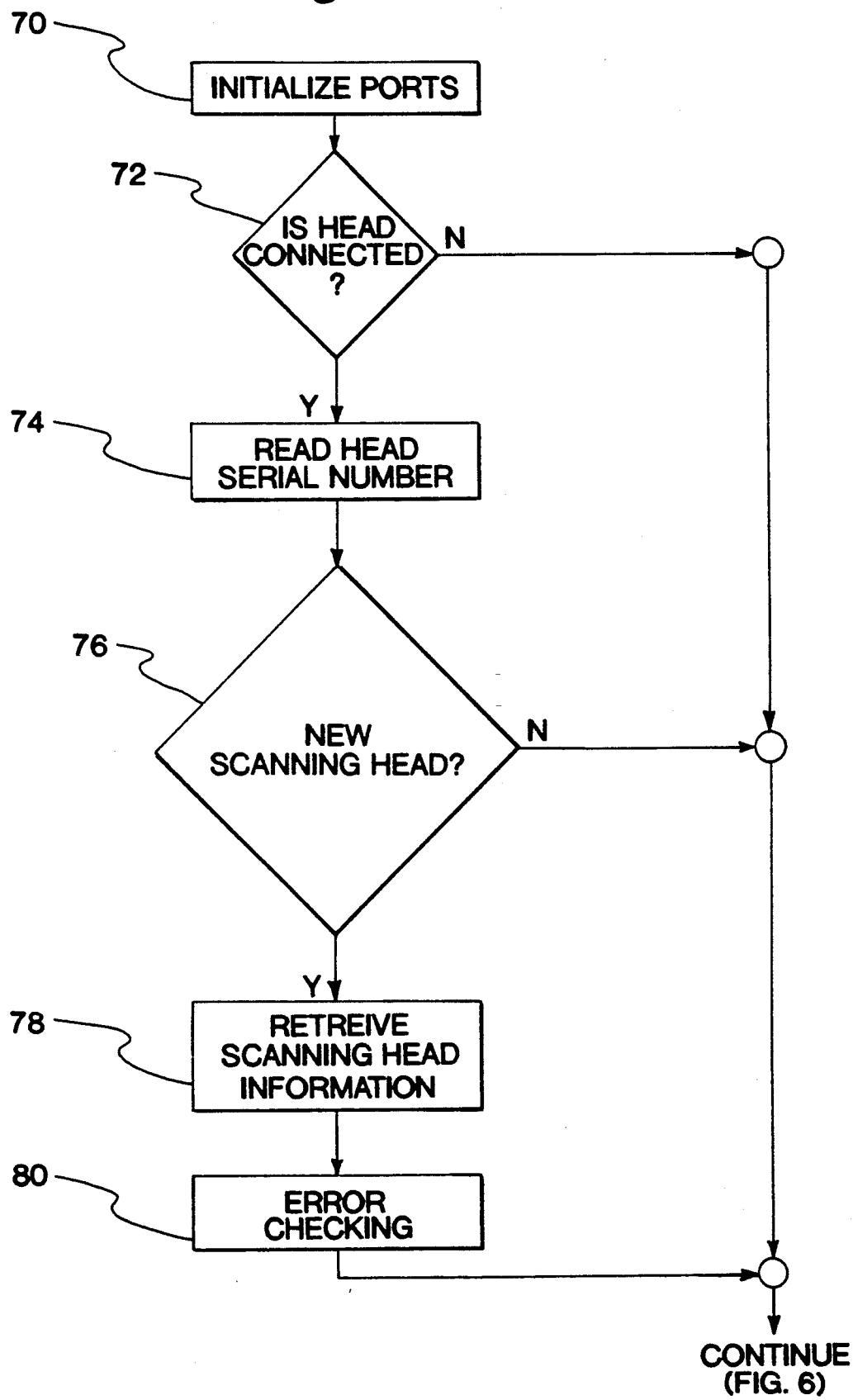
FIG. 5 is a flow diagram showing the major functions performed by the CPU to insure that one of the interchangeable scanner heads is properly connected and is operable.

FIG. 5 illustrates the operational flow of the software for controlling the CPU 12. When the modular base unit 10 is turned on, a boot up sequence is followed to insure the unit is operating correctly and that there is a scanning head 28, 29 or 30 attached. Boot-up begins with initialization 70 of the I/O ports 42. This consists of setting each of the port bits to their default values. The next step 72 is to determine if one of the interchangeable scanning heads 28, 29 or 30 is connected to the base unit 10. Determination of the connection of a selected one of the scanning heads 28, 29 or 30 is accomplished by means of reading the analog voltage level from the selected scanning head 28. If the voltage is greater than a predetermined value, then a scanning head is not connected. Another method to determine if a scanning head is present would be to examine the bit level of a selected line.

Figure 9:
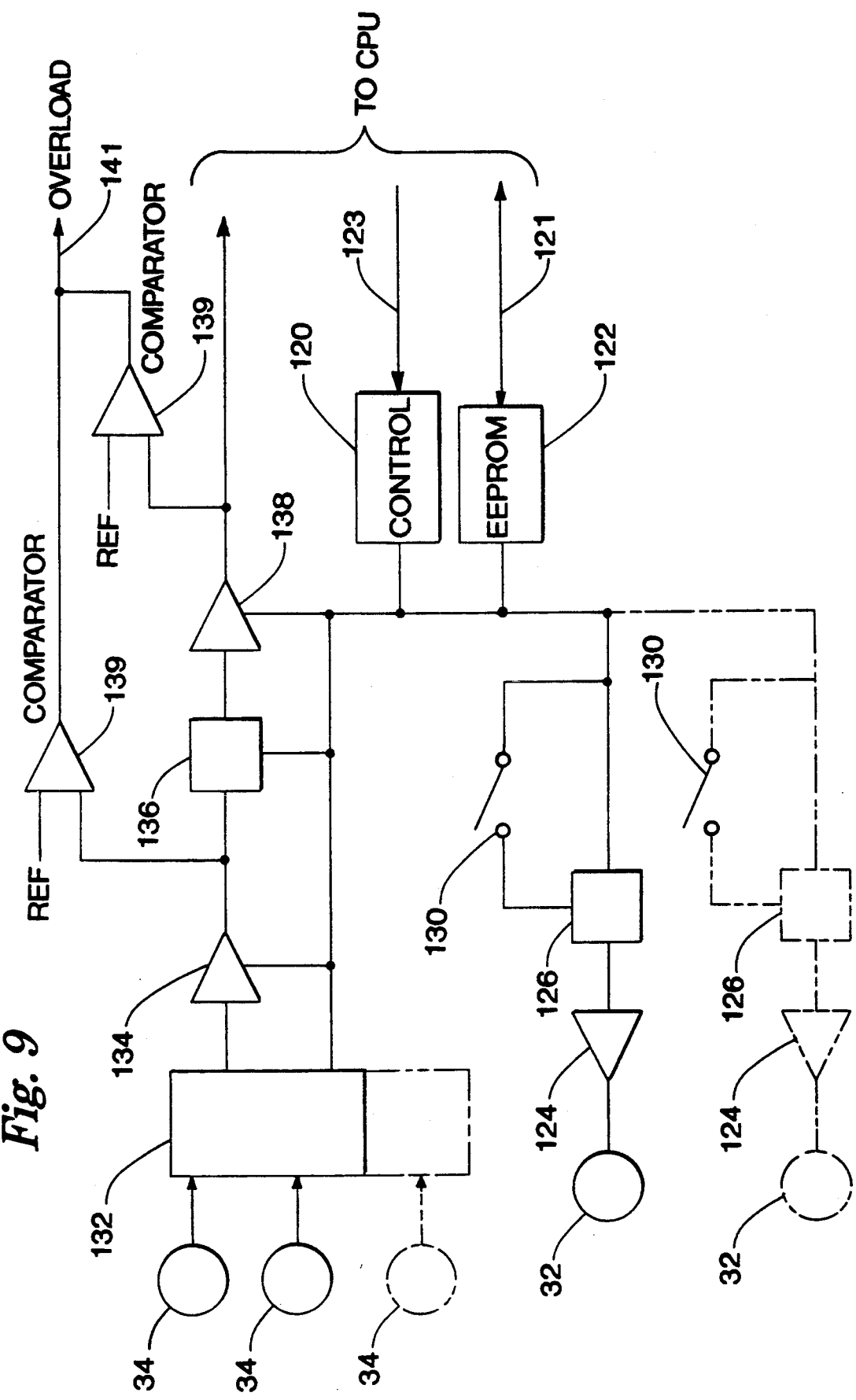
FIG. 9 is a block diagram showing the major components of the light source, detectors and other electronics associated with one of the scanning heads for the present invention.

If a scanning head 28, 29 or 30 is connected, then the next step 74 is to read the serial number of the selected scanning head 28. This is done by reading the serial number stored in a scanning head EEPROM 122 (FIG. 9). The next step 76 is to determine if the selected scanning head 28 is the same as the previous one used. If yes, then the program can continue to obtain data in the manner described in FIG. 6. If a different interchangeable scanning head 29 or 30 has been attached, or if this is the first measurement being taken since the base unit 10 was powered up, then data stored in the scanning head EEPROM 122 must be transferred to the static RAM 16 in the base unit 10 at step 78. The data retrieved from the EEPROM 122 during step 78 represents information sufficient for mathematically describing the physical characteristics of the particular scanning head 28, 29 or 30. This information includes the physical locations of source 32 and detector 34 mounting locations, as well as calibration constants and other information about optical characteristics of the scanning head 28, 29 or 30 the source 32, and the detector 34.

It is will be recognized that it is important that all data be accurately transferred between the selected scanning head 28 and the base unit 10. In the preferred embodiment, Error checking 80 is accomplished using a checksum method. Other error checking schemes could also be employed such as cyclic redundancy checks. If the data from the selected scanning head 28 has been transferred successfully, then the boot-up procedure is completed. If a data transfer error occur, then a HEAD ERROR diagnostic is reported on the LCD 22 and the CPU 12 prevents access to measurement features.

Figure 6:
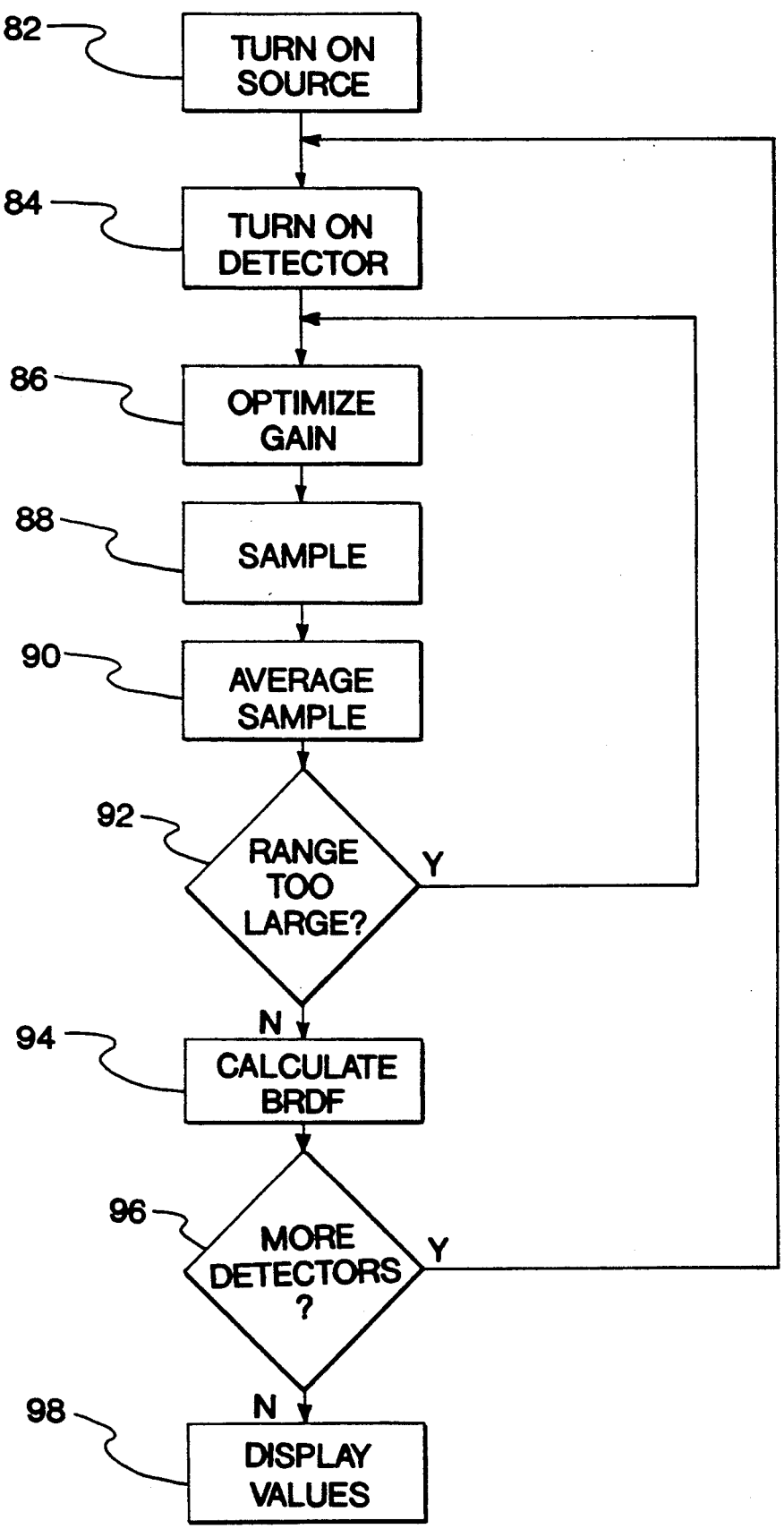
FIG. 6 is a flow diagram showing the major functions performed by the CPU during a measurement process.

With reference now to FIG. 6, the operational flow for taking the BRDF measurements with the present invention will be described. FIG. 6 illustrates the software functions that perform the calculation and display of BRDF measurement results. Information transferred to the CPU 12 during the boot-up phase includes scanning head 28 information such as the number of sources 32 and the number of detectors 34 in the selected attached scanning head 28. The preferred embodiment allows for from 1 to 3 light sources 32, and from 1 to 8 detectors 34 to be contained within the scanning head 28. The first step 82 is to select and turn on the selected light source 32. The second step 84 is to select and turn on one or more selected detectors 34 in this scanning head 28. Selection and turning on of light sources 32 and detectors 34 is achieved by transferring the proper control word from the base unit 10 to the selected scanning head 28.

The next step 86 is to set the optimal maximum gain of the first detector 34. The amount of reflected light varies from sample to sample. The preferred embodiment utilizes both pre and post linear gain amplification stages. Combinations of these amplifiers allows gains to be set by the base unit 10 from 0 to 80 db in 10 db steps. Another way to obtain amplification is to utilize logarithmic gain stages. After the gains are set, then sampling 88 occurs. Samples are taken every T seconds for N seconds where T and N are chosen to minimize the effects of noise. The average 90 of these samples is computed. At step 92, the range of the resulting data samples are examined to see if they fall within the range of the A/D 40 without clipping. The range of the A/D 40 means of the preferred embodiment is 1-254. If gain settings are satisfactory, then the actual BRDF calculation for the selected detector 34 are made at step 94 using the information and coefficients previously transferred from the EEPROM 122 in the scanning head 28. At step 96, a determination is made as to whether more detectors need to be read based upon the number of detectors present for the selected scanning head 28. If so, the program repeats starting with detector turn on 84 and continues the measurement process until all detector values have been processed for the selected scanning head 28. When all readings have been made, then values are displayed at step 98 on the LCD 22 and stored in the static RAM 16 if desired.

Figure 7:
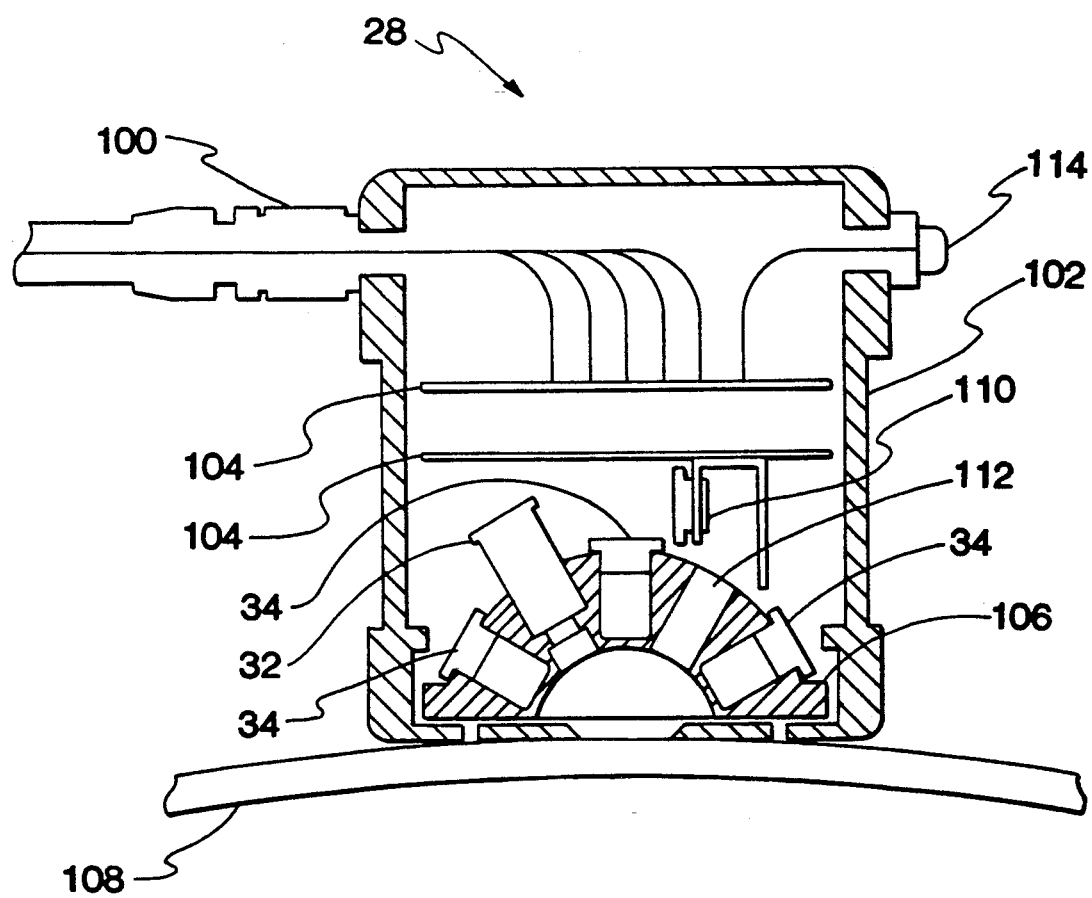
FIG. 7 is a cut-away view of one of the interchangeable scanning head assemblies of FIG. 1.

FIG. 7 shows a cut-away view of one of several selectable interchangeable scanning heads 28. The selected one of the scanning heads 28, 29 or 30 is connected to the base unit 10 by a universal cable 38. The universal cable 38 consists of 12 conductors with 12 pin male connectors 100 on each end. Referring to FIG. 7 it is seen that the containing means for this example of the preferred embodiment consists of a cylindrical aluminum housing 102 which contains the electronics assembly 104, and a non-conducting, opaque detector/source mount 106. As many as three light sources 32 and as many as 8 detectors 34, can be mounted in a selected version of the source mount 106. The detector/source mount 106 is mounted on springs to the cylinder 102 to allow the operator to precisely position the head on curved surfaced samples 108 to be measured. In the scanning head 28 shown in FIG. 7, only one source 32 is used. A typical source 32 could be a 670 nm laser diode. Other sources 32, such as infrared diodes, are also usable depending upon the desired application.

Light from the source 32 is reflected from the sample surface 108 through the beam dump opening 112 to the beam dump detector 110. Measurements of the beam at the beam dump 110 are taken for reflectance calculations. The purpose of beam dumping is to remove the specular beam from the inner volume of the source/detector housing 106. This allows measurement of only scattered light by removing all purely reflected light. Light scattered from the surface is measured by one or more detectors 34 placed at locations around the surface of the source/detector mount 106. In this embodiment of the scanning head 28, source 32 and detectors 34 are mounted at 30 degree angle spacing from the vertical for the particular geometry of this unit. Other spacings can be chosen for this or other size scanning head 28. This particular embodiment of scanning head 28 is designed to be hand-held. There is a measurement switch 114 which can be operated to cause readings to be taken each time the switch is operated.

Figure 8:
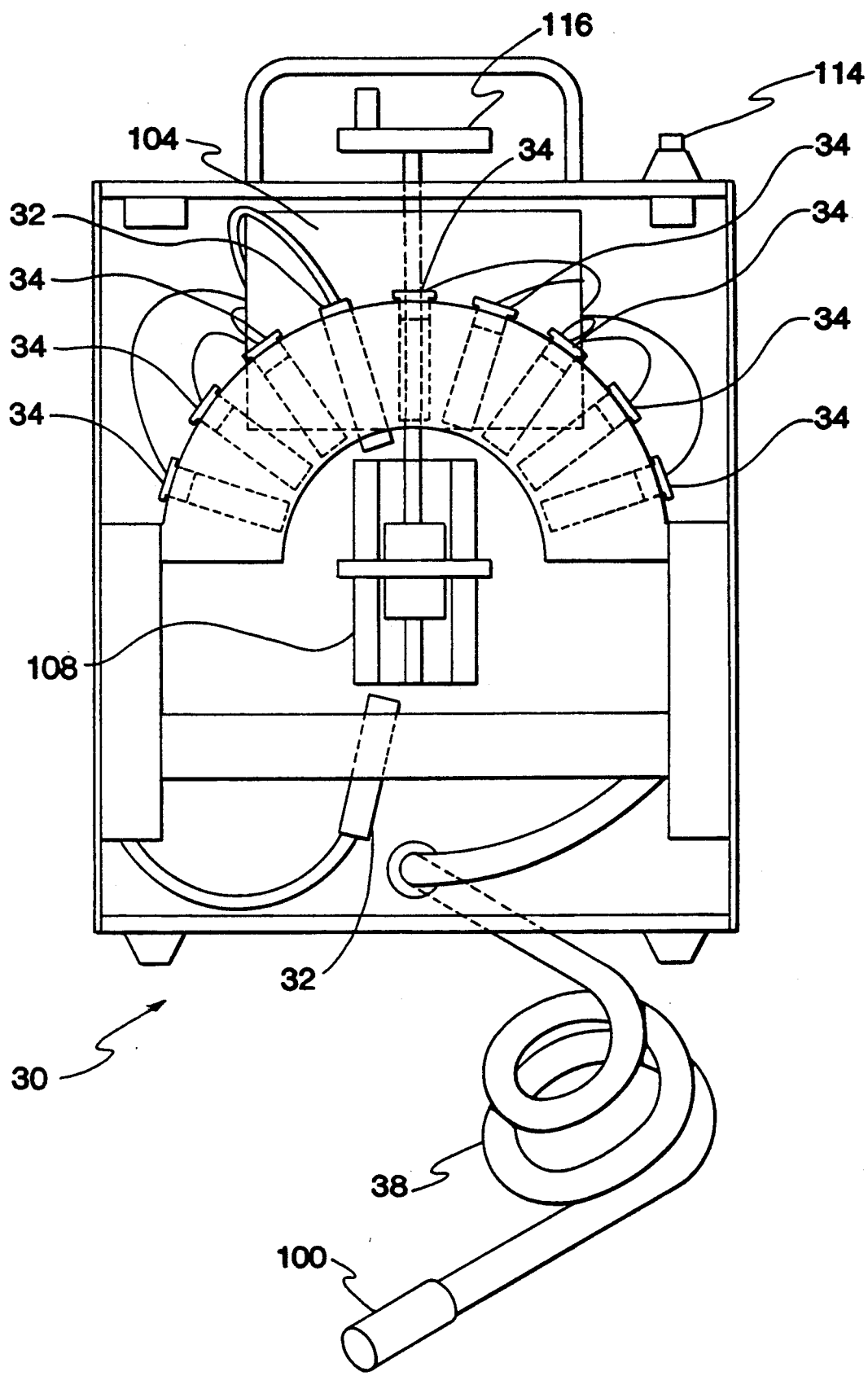
FIG. 8 is a pictorial view of a larger scanning head in which the sample is placed inside a light shielding box.

FIG. 8 is another version of an interchangeable scanning head 30. This scanning head 30 connects to the base unit 10 via the universal cable 38. The function of this scanning head 30 is to measure scatter from samples which are placed inside it. Detectors 34 can be mounted in several positions, and the sample 108 height can be varied by the sample height adjustment 116. The remote trigger 114 causes measurements to be recorded and transmitted to the base unit 10. Electronics boards 104 provide the same functions as those described for FIGS. 7 and 9.

FIG. 9 is a block diagram showing the functions performed by electronics boards 104 or electronic interface circuit card 36 located in each of several selectable scanning heads 28, 29, 30 of the present invention. Communications between the base unit 10 and a selected scanning head 28 are handled by the control circuits 120. Configuration information for a selected scanning head 28 is contained in the EEPROM memory 122. Configuration information which includes scanning head serial number and configuration of sources and detectors, is transferred to the base unit 10 via a serial data circuit 121 on the universal cable 38. A second serial data circuit 123 provides transfer of other commands from the base unit 10 to a selected scanning head 28. These commands include "Source On," "Detector Select," and "Gain Select." Commands from the base unit 10 received by a selected scanning head 28 are decoded in the control 120 section by two eight-bit shift registers.

The command to initiate a scatter measurement is comprised of a sequence of individual control functions. First, a source 32 is turned on. Each source 32 has its own driver 124. In this embodiment, an operational amplifier driving a bipolar junction transistor is utilized, although it will be recognized that several other devices that can be used to drive these sources. The driver circuit 124 contains an adjustable regulator, designed to provide constant source 32 output intensity with varying supply voltages levels and to compensate for variations among individual sources 32. The modulator 126 applies square wave modulation to the driver 124 at about 600 Hz, with a duty cycle of about 50%. The square wave is produced by a mono-stable multi-vibrator. A second output from the modulator 126 is used as a phase reference by the filter section 136. The modulator 126 also contains a switch 130 to allow the source 32 to be manually operated continuously without modulation for source alignment purposes.

Direct light from the source 32, or scattered light from the sample is received by one or more detectors 34. The detector 34 that will be used for the measurement is selected by the commands from the base unit 10 as decoded by the control 120 and sent to the multiplexer 132. Unused detectors 34 are shorted and grounded to reduce circuit noise. Although the preferred embodiment utilizes a multiplexer 132, it should be noted that there are other ways to provide for selection of the detector 34. For example, each detector 34 could have its own amplifier 134, filter 136, and final amplifier 138.

Analog voltage from the selected detector 34 is routed to an amplifier 134. The current-sense signal from the detector 34 is converted to a voltage-sense signal, and amplified by four cascaded stages of an operational amplifier. The fourth of these stages is configured for two discrete values of gain, controlled by signals from the control 120. The filter 136 uses a phase reference signal from the modulator 126 section to provide an extremely selective filtering action. The filter 136 also uses an operational amplifier. In addition, the gain of the filter 136 section is controlled by the base unit 10 command routed to control 120. The final amplifier 138 uses an operational amplifier. Two discrete values of gain may be selected by a signal from the base unit 10 via a command to control 120. The signal level is sampled at two points in the signal path. These two samples are applied to separate sections of a comparator 139. which provides an overload signal 141 to the base unit 10 if the gain settings are too large. This allows the CPU 12 to set the optimum amount of gain for the received signal. The detector 34 output signal is referenced to an analog ground, different in potential from the logic and power supply grounds. This allows a definite value to be defined for zero received signal.

In this embodiment, the EEPROM 122 memory is a type 24C16I from Xicor, Inc of Milpitas, CA. Shift registers used are 74HC595 such as from National Semiconductor Corporation of Santa Clara, CA. The TLC555ID multi-vibrator, TLC2201BID and TLC2654 operational amplifiers and TLC3541D comparators are all from Texas Instruments, Inc of Dallas, Tx. Solid state analog switches used are DG403DY available from Siliconix of Santa Clara, CA.

Figure 10:
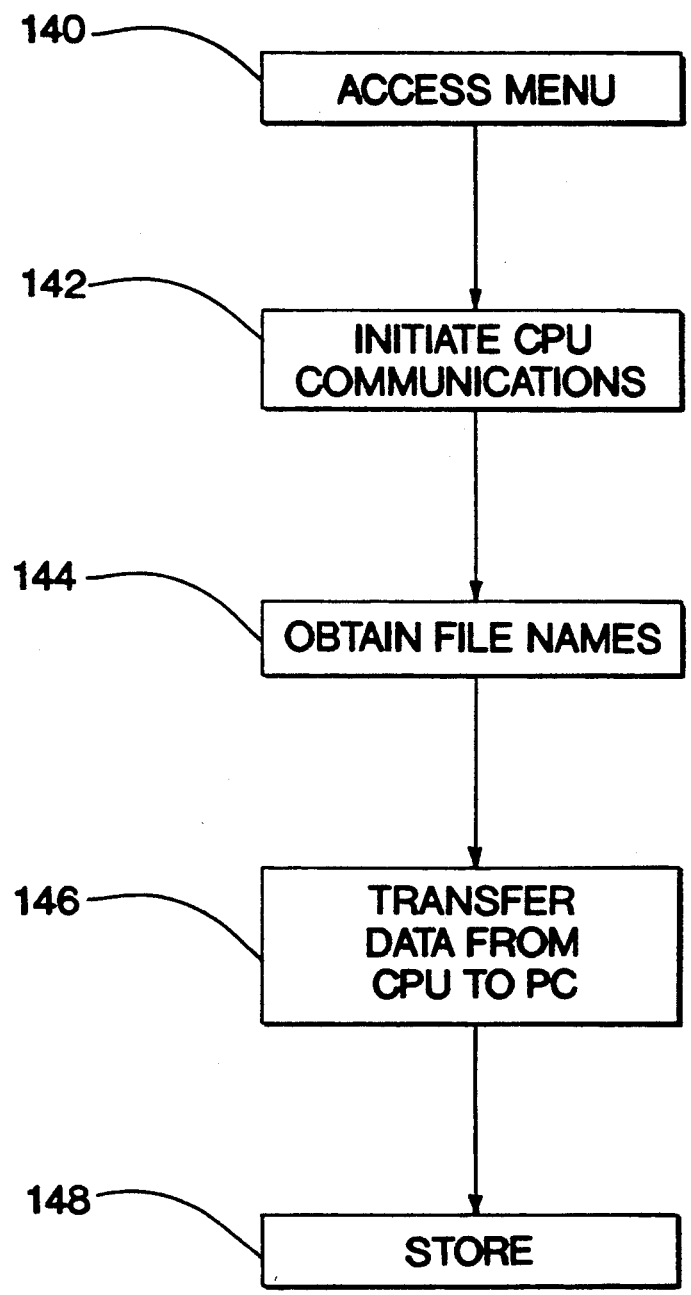
FIG. 10 is a flow diagram showing the operational flow for information transfer between the CPU and a PC.

FIG. 10 shows the operational flow for information transfer between the base unit 10 and the PC 50 of the alternate embodiment. The first function 140 is to use the multi-keypad 20 to obtain access to the serial port menu. The next step 142 is to initiate base unit 10 to PC 50 communications. The PC 50 sends as ASCII character to notify the base unit 10 that it is ready for data transfer. The next operational function 144 is to read the list of measurement sample file names stored in the base unit 10. In the preferred embodiment, there can be as many as 255 files, with as many as 255 measurements stored in each named file. Information transfer 146 from the base unit 10 to the PC 50 can include base unit 10 unit number, scanning head source and or detector angles, previously saved BRDF measurements, and time/date information. It will be recognized, however, that any information applicable to this or other applications of this embodiment which is stored in the base unit 10 can be transferred to the PC 50. This information can then be analyzed or otherwise used by programs stored in the PC 50.

Although the description of the preferred embodiment has been presented, it is contemplated that various changes could be made without deviating from the spirit of the present invention. Accordingly, it is intended that the scope of the present invention be dictated by the appended claims rather than by the description of the preferred embodiment.

We claim:

1. A modular scatterometer for measuring light scatter from a subject surface comprising:
    a base unit, including:
        means for supplying electrical power to the scatterometer;
        processor means for controlling operational flow of various functions of the scatterometer and for analyzing light scatter measurements; and
        operator control means for providing control information to the processor means relating to the operational flow of the scatterometer;
    a scanning head selected from a plurality of interchangeable scanning heads, the selected scanning head being operatively connected to the base unit, each of the interchargeable scanning heads being detachably connectable to the base unit and each of the interchangeable scanning heads including:
        one or more light source means for generating a light beam that is incident upon the subject surface;
        one or more detector means for detecting light scattered from the subject surface by the light beam; and
        means for storing profile information that describes certain characteristics and parameters associated with the interchangeable scanning head; and
    transmission means operably connected to the base unit and the selected scanning head for transmitting and receiving both analog and digital signals between the selected scanning head and the base unit.

2. The modular scatterometer of claim 1 wherein the light scatter measurements are analyzed using a bidirectional reflective distribution function.

3. The modular scatterometer of claim 1 wherein the base unit further comprises:
    a display means operably connected to the base unit and the processor means for displaying operator information; and
    an input/output port means operably connected to the processor means for transmitting information including light scatter measurements to a remote computer processor.

4. The modular scatterometer of claim 1 wherein the interchangeable scanning head further comprises a beam dump means at the position of the specular component of the light beam as reflected from the subject surface and operably connected with the control means for measuring the intensity of the light beam as reflected from the subject surface.

5. The modular scatterometer of claim 4 wherein the light scatter measurements are analyzed using a bidirectional transmissive distribution function.

6. The modular scatterometer of claim 1 wherein the detector means detects light as power and converts the power into an analog electrical signal.

7. The modular scatterometer of claim 6 wherein the analog electrical signals are sent to the base unit via the transmission means and the base unit further comprises an analog-to-digital conversion means for converting the analog electrical signal to a digital signal representing the light detected by the detector means.

8. The modular scatterometer of claim 6 wherein the selected scanning head further comprises an analog-to-digital conversion means for converting the analog electrical signals to a digital signal representing the light detected by the detector means that is then transmitted to the base unit via the transmission means.

9. An interchangeable scanning head for a modular scatterometer for measuring light scatter from a subject surface and for transmitting light measurements to a base unit for processing, the scanning head comprising:
    one or more light source means for generating a light beam that is incident upon the subject surface;
    one or more detector means for detecting light scattered from the subject surface by the light beam;
    means for storing profile information that describes certain characteristics and parameters associated with the interchangeable scanning head;
    means for detachably connecting the scanning head to the base unit so that the interchangeable scanning head can be replaced with one or more other interchangeable scanning heads having different characteristics and associated parameters; and
    control means operably connected with the base unit, the light source means, the detector means, and the means for storing profile information for controlling the operation of the scanning head in response to commands from the base unit and for transmitting commands to and from the base unit and for transmitting measurements of light scattered from the subject surface as detected by the detector means and profile information as stored by the means for storing profile information to the base unit.

10. The scanning head of claim 9 wherein the scanning head is portable and hand-held.

11. The interchangeable scanning head of claim 9 further comprising beam dump means at the position of the specular component of the light beam as reflected from the subject surface and operably connected with the control means for measuring the intensity of the light beam as reflected from the subject surface.

12. The interchangeable scanning head of claim 9 wherein the detector means detects light as power and converts the power into an analog electrical signal.

13. A modular scatterometer for measuring light scatter from a subject surface comprising:
 a base unit, including:
  means for supplying electrical power to the scatterometer;
  processor means for controlling operational flow of various functions of the scatterometer and for analyzing light scatter measurement information; and
  operator control means for providing control information to the processor means relating to the operational flow of the scatterometer;
 a scanning head detachably and operatively connected to the base unit, the scanning head including:
  one or more light source means for generating a light beam that is incident upon the subject surface;
  one or more detector means for detecting light scattered from the subject surface by the light beam; and
  means for storing profile information that describes certain characteristics and parameters associated with the scanning head; and
 transmission means operably connected to the base unit and the scanning head for transmitting and receiving both analog and digital signals between the scanning head and the base unit.

14. The modular scatterometer of claim 13 wherein the processor means analyzes the light scatter measurement information by using a bidirectional reflective distribution function.

15. The modular scatterometer of claim 13 wherein the scanning head further comprises beam dump means at the position of the specular component of the light beam as reflected from the subject surface and operably connected with the control means for measuring the intensity of the light beam as reflected from the subject surface.

16. The modular scatterometer of claim 13 wherein the detector means detects light as power and converts the power into an analog electrical signal.

17. The modular scatterometer of claim 16 wherein the analog electrical signals are sent to the base unit via the transmission means and the base unit further an analog-to-digital conversion means for converting the analog electrical signal to a digital signal representing the light detected by the detector means.

18. The modular scatterometer of claim 16 wherein the scanning head further comprises an analog-to-digital conversion means for converting the analog electrical signal to a digital signal representing the light detected by the detector means that is then transmitted to the base unit via the transmission means.

19. The modular scatterometer of claim 13 wherein the scanning head is portable and hand held.

* * * * *